United States Patent [19]

Bajpai

[11] Patent Number: 4,778,471

[45] Date of Patent: Oct. 18, 1988

[54] ZCAP CERAMICS

[75] Inventor: Praphulla K. Bajpai, West Carrollton, Ohio

[73] Assignee: University of Dayton, Dayton, Ohio

[21] Appl. No.: 932,742

[22] Filed: Nov. 19, 1986

[51] Int. Cl.$^4$ ................................. A61F 2/28
[52] U.S. Cl. ........................... 623/16; 623/11; 623/66; 433/201.1; 501/1; 106/35; 128/92 YQ
[58] Field of Search ............... 433/201.1; 623/11, 16, 623/56, 16 B, 16 D, 16 F; 501/1; 106/35, 286.6; 128/92 YQ; 604/890, 894

[56] References Cited

U.S. PATENT DOCUMENTS

| | | | |
|---|---|---|---|
| 3,655,605 | 4/1972 | Smith et al. | 106/35 |
| 3,984,914 | 10/1976 | Schwartz | 623/16 |
| 4,097,935 | 7/1978 | Jarcho | 3/1.9 |
| 4,149,893 | 4/1979 | Aoki et al. | 106/35 |
| 4,191,740 | 3/1980 | Heusser et al. | 623/16 |
| 4,192,021 | 3/1980 | Deibig et al. | 3/1.9 |
| 4,218,255 | 8/1980 | Bajpai et al. | 106/45 |
| 4,243,567 | 1/1981 | Potter | 523/116 |
| 4,250,277 | 2/1981 | Maries et al. | 106/35 |
| 4,330,514 | 5/1982 | Nagai et al. | 423/309 |
| 4,376,168 | 3/1983 | Takani et al. | 501/1 |
| 4,431,451 | 2/1984 | Mabie et al. | 433/201.1 |
| 4,548,959 | 10/1985 | Nagai et al. | 523/115 |
| 4,554,686 | 11/1985 | Baker | 623/16 |
| 4,604,097 | 8/1986 | Graves, Jr. et al. | 623/11 |

FOREIGN PATENT DOCUMENTS

| | | | |
|---|---|---|---|
| 0058867 | 9/1982 | European Pat. Off. | 623/16 D |
| 0171546 | 9/1984 | Japan | 623/16 |

OTHER PUBLICATIONS

Graves, G. A. et al., "Resorbable Ceramic Implants," *J. Biomed. Mater. Res. Symp.* 2 (*Part I*): 91, 1972.

*Primary Examiner*—Richard J. Apley
*Assistant Examiner*—Paul B. Prebilic
*Attorney, Agent, or Firm*—Biebel, French & Nauman

[57] ABSTRACT

The present invention replaces the aluminum oxide in ALCAP ceramics with zinc oxide or zinc sulfate or mixtures thereof to provide a resorbable high strength ceramic. Specifically, a zinc bioceramic is provided comprising about 10 to 50 wt. % zinc oxide or zinc sulfate or mixtures thereof, about 30 to 40 wt. % calcium oxide and about 10 to 40 wt. % phosphorus pentoxide.

The zinc based ceramics of the present invention can be used in many of the same applications as hydroxyapatites, tricalcium phosphates and ALCAP ceramics. When mixed with a setting agent, the zinc based ceramics of the present invention are useful as surgical cements or grouts. The zinc based ceramics are also useful as hard tissue substitutes in orthopedic, dental and maxillofacial surgeries and as drug delivery devices.

21 Claims, No Drawings

ZCAP CERAMICS

BACKGROUND OF THE INVENTION

The present invention relates to zinc based bioceramics, and more particularly, to zinc based ceramic surgical cements or grouts and in vivo implants.

Ceramic materials which are useful as drug delivery devices and as hard tissue substitutes in orthopaedic, dental and maxillofacial surgeries include hydroxyapatites, tricalcium phosphates (TCP) and partially resorbable alumino-calcium oxide-phosphorus pentoxide (ALCAP) ceramics. U.S. Pat. Nos. 4,097,935 to Jarcho; 4,149,893 to Aoki et al.; and 4,330,514 and 4,548,959 to Nagai et al. disclose hydroxyapatite ceramics. U.S. Pat. No. 4,192,021 to Deibig et al. discloses calcium phosphates.

U.S. Pat. No. 4,218,255 to Bajpai et al. and Graves, G. A. et al., "Resorbable Ceramic Implants," J. Biomed. Mater. Res. Symp. 2(part I): 91, 1972, disclose ALCAP ceramics. These ceramics are obtained by mixing calcium oxide, aluminum oxide and phosphorus pentoxide in weight ratios of about 35–40% CaO, about 45–55% $Al_2O_3$ and about 10–20% $P_2O_5$; powdering the mixture and calcining. A typical ALCAP ceramic is prepared from a 38:50:12 by weight mixture of calcium oxide, aluminum oxide and phosphorus pentoxide which is calcined at 2400° F. for twelve hours and ground.

U.S. Pat. No. 4,376,168 to Takami et al. relates to sintered calcium phosphate ceramics which are useful as replacements for bones or teeth. In one embodiment, the ceramic is prepared using a frit comprising $P_2O_5$ and one or more metal oxides selected from the group consisting of BaO, CaO, MgO, ZnO, $Na_2O$, and $K_2O$. About 0.5 to 15% of the frit is admixed with a calcium phosphate starting material such as apatite. The compacted mass of the resultant mixture is then sintered. In Table 5, frit example C comprises $P_2O_5$, CaO, and ZnO (47:44:9 mol ratio; 68:25:7 wt. ratio).

ALCAP ceramics are advantageous because they are resorbable and stronger than apatite and TCP. However, while there is no evidence that ALCAP ceramics are toxic, aluminum has been implicated in neural and bone disorders and this has cast a shadow on the use of ALCAP ceramics in humans. Thus, a need exists for a resorbable aluminum-free ceramic useful in dental and orthopaedic applications.

SUMMARY OF THE INVENTION

The present invention replaces the aluminum oxide in ALCAP ceramics with zinc oxide or zinc sulfate or mixtures thereof to provide a resorbable high strength ceramic. Zinc is an essential element of the body and is required in daily diet. A deficiency of zinc causes pathogenesis in both humans and animals. Zinc controls lipid peroxidation in the liver and erythrocytes and is necessary for maintaining a normal concentration of vitamin A. Zinc amalgams are well tolerated by hard tissues and allow growth of bone within six to twelve weeks. Also, good evidence exists that zinc is involved in the process of wound healing.

The zinc based ceramics of the present invention can be used in many of the same applications as hydroxyapatites, tricalcium phosphates and ALCAP ceramics. When mixed with a setting agent, the zinc based ceramics of the present invention are useful as surgical cements or grouts. The zinc based ceramics are also useful as hard tissue substitutes in orthopaedic, dental and maxillofacial surgeries and as drug delivery devices.

Thus, an object of the present invention is to replace the aluminum oxide in alumimum based ceramics with zinc oxide to provide a ceramic having the properties of an aluminum based ceramic and which is resorbable but without the potential toxic side effects of aluminum.

A further object of the present invention is to provide a zinc based ceramic which can be mixed with a setting agent to provide a surgical cement or grout.

Another object of the present invention is to provide a zinc based ceramic which is useful as a hard tissue substitute in orthopedic, dental and maxillofacial surgeries and as a drug delivery device.

In accordance with the present invention, a bioceramic is provided comprising about 10 to 50 wt. % zinc oxide or zinc sulfate or mixtures thereof, about 30 to 40 wt. % calcium oxide and about 10 to 40 wt. % phosphorus pentoxide. In the preferred embodiment, the ceramic is totally resorbable.

In accordance with another embodiment, the present invention provides a surgical cement or grout composition comprising a powdered bioceramic and a setting agent.

The present invention also provides an implant comprising greater than about 10 to 50 wt. % zinc oxide or zinc sulfate or mixtures thereof, about 30 to 40 wt. % calcium oxide and about 10 to 40 wt. % phosphorus pentoxide, said implant being essentially non-toxic and bioabsorbable.

Other objects and advanrages of the present invention will be apparent from the following description and the appended claims.

DETAILED DESCRIPTION OF THE INVENTION

The ceramic of the present invention comprises about 10 to 50 wt. % zinc oxide or zinc sulfate or mixtures thereof, about 30 to 40 wt. % calcium oxide and about 10 to 40 wt. % phosphorus pentoxide. Preferably, the ceramic comprises about 30 to 50 wt. % zinc oxide, about 30 to 40 wt. % calcium oxide and about 20 to 40 wt. % $P_2O_5$. The amount of $P_2O_5$ must be carefully controlled. If the phosphorus pentoxide percentage exceeds about 40%, upon calcining, the composition melts to a glassy material rather than calcining evenly.

The composition of the preferred bioceramic varies with the end use. Preferably, for use as a solid ceramic and as a powdered ceramic in a cement or grout, the composition comprises about 50 wt. % ZnO, about 30 wt. % CaO and about 20 wt. % $P_2O_5$. Preferably, for use as a drug delivery device, the composition comprises about 30 wt. % ZnO, about 40 wt. % CaO and about 30 wt. % $P_2O_5$.

Zinc oxide can be replaced by zinc sulfate or used in combination with zinc sulfate. Sulfate is a normal bone component. A sulfate addition hastens the setting time and provides a ceramic which resorbs relatively quickly. An example of an useful ceramic in which zinc oxide is replaced by zinc sulfate is 48 wt. % $ZnSO_4$, 32 wt. % CaO and 20 wt % $P_2O_5$. An example of an useful ceramic in which zinc oxide is used in combination with zinc sulfate is 24 wt. % $ZnSO_4$, 24 wt. % ZnO, 32 wt % CaO and 20 wt. % $P_2O_5$. It is also believed that the foregoing result can be achieved using ZnO in combination with calcium sulfate. An example of an useful ceramic in which zinc oxide is used in combination with calcium sulfate is 48 wt. % ZnO, 32 wt. % CaSO$_4$ and 20 wt. % P$_2$O$_5$.

To prepare the ceramics of the present invention, the oxides, in powder form, are mixed and compressed under a pressure of about 2000 to 20,000 lbs total load. The mixture is then calcined at about 700° C. to 1300° C. for about 24 to 36 hours.

The calcined composition is again powdered by grinding and controlled in size by passing the mixture through mesh screens. The particle size of the bioceramic varies with the end use. For drug delivery systems, the ceramic has a particle size of about 1 to 38 microns. Typically, for a cement or grout, the ceramic has a particle size of about 1 to 400 microns. For a bone implant device, the ceramic has a particle size of about 40 to 200 microns.

The powdered ceramic can be mixed with a setting agent to provide a surgical cement or grout. The ratio of the ceramic to the setting agent varies depending upon the cement's or grout's application. Some applications require more or less viscous compositions while others require faster or slower setting times. Typically, the ratio of the ceramic to the setting agent based on the weight (solids) of the surgical cement composition is about 1:1 to 3:1, and preferably, about 1:1 to 2:1.

Any conventionally used surgical cement setting agent can be used in the present invention. Particularly useful setting agents include amines, amino acids, polyfunctional carboxylic acids, polymers which are reactive with the ceramic and mixtures thereof.

Examples of useful amines include carbodiimides; N,N-dimethyl-p-toluidine; N,N-diethyl-p-toluidine; N,N-dimethylaniline; N,N-diethylaniline and mixtures thereof.

Examples of useful amino acids include alanine, arginine, asparagine, cysteine, glutamine, glycine, histidine, isoleucine, leucine, lysine, methionine, phenylalanine, proline, serine, threonine, valine and mixtures thereof.

Examples of useful polyfunctional carboxylic acids include aconitic, alpha-ketoglutaric, citraconic, citric, fumaric, glutaconic, itaconic, maleic, malic, pyruvic, oxalic, succinic, tartaric and mixtures thereof. Particularly preferred acid are alpha-ketoglutaric and malic acid. These acids are typically characterized by 6 to 10 carbon atoms and 2 to 4 carboxyl groups.

Examples of useful polymers include polylactic acid, polymethacrylic acid and polyacrylic acid. These polymers are capable of chelating with the zinc and/or calcium atoms in the ceramic.

Antibiotics can be added to the cement in order to prevent and/or treat infection.

If the pH of the cement is acidic, for example 5-6, to neutralize the composition, bases such as KOH, NaOH, Ca(OH)$_2$, Zn(OH)$_2$, and buffering agents can be added.

The surgical cement or grout composition of the present invention can be formulated as a two-part package of the porous resorbable ceramic material and the setting agent which are mixed prior to surgery, or as a pre-mixed one-part mixture of the ceramic material and the setting agent. To cure the surgical cement or grout composition, the composition is mixed with water or water-containing medium. When water is added to the composition, two setting stages are observed. During the first stage, the viscosity of the mixture increases rapidly and a paste is obtained which can be worked into a desired shape. During the second stage, the composition sets. While in most instances, the compositions will be mixed with distilled or deionized water and formed into a paste for application, occasionally it may be desirable to mix the cement or grout composition with blood or serum. In this regard, the cement composition of the present invention has excellent hemostatic properties.

In some situations, metal salts may be added to the cement compositions to enhance the cure rate. Calcium salts, and more particularly, calcium chloride and calcium sulfate are particularly useful for this purpose. When used, the salts are usually added in an amount of about 5-20% by weight.

Oily materials such as Vitamin D or E can be added to the cement or grout composition. Typically, these materials are oily so that a cement having a paste consistency results.

The surgical cement or grout compositions of the present invention can be used in orthopaedic, oral and maxillofacial surgery. The compositions can be used in making bone grafts, bone scaffolds, bone replacements or prostheses such as bone plates and the like.

To be used as a preformed implant or ceramic block to repair load bearing as well as non-load bearing traumatized bone, the ceramic is usually formed into a green shape by mixing the powdered ceramic with a binder such as polyvinyl alcohol, compressing the mixture in a die and sintering. Other useful binders include hypoimmunogenic collagen, fibrin and hyaluronic acid. Typically, the weight ratio of the powdered ceramic to the binder is about 97.5:2.5 to 70:30. The mixture is compressed at a pressure of about 2000 to 20,000 lbs. The green shaped composition is then sintered at a temperature of about 1200° C. to 1500° C. for about 24 to 48 hours.

The ceramic particle size, amount of binder and the sintering temperature determine the final pore size of the implant. Pore size may range from about 1 to 400 microns. The resorption rate is directly related to the pore size when the ceramic composition is totally resorbable.

In accordance with another embodiment, the compressive strength of the sintered ceramic block can be increased several fold by impregnating the blocks in polylactic acid, polyglycolic acid or polycaprolactone dissolved in chloroform or methylene chloride.

The preformed implants and cements of the present invention can be used in orthopaedic, oral and maxillofacial surgeries.

The foregoing procedure can also be used to form hollow cylinders or other shapes useful as pharmaceutical carriers. The porous resorbable ceramic material is capable of controlling the critical release of pharmaceuticals such as proteins, polypeptides, hormones, antibiotics, bacteriostats, and other large molecular weight materials within the physiological environment, i.e., the living body. In using a hollow cylinder, the ends of the cylinder can be sealed with a medical adhesive. The ceramic's microstructure (having the aforementioned pore size) allows for the release of the pharmaceuticals. The released material flows or diffuses from the hollow center through the pore structure of the ceramic carrier to the exterior surface and into the physiological body fluids. The release rate of the drug, chemical, etc., is therefore, partially dependent on the ceramic microstructure.

In accordance with another embodiment, the delivery rate of contents enclosed within sintered ceramic drug delivery device or implant can be decreased by impregnating the sintered ceramic with a polymer such as poly(lactic acid), polyglycolic acid, and/or polycaprolactone.

The drug-containing ceramic is implanted subcutaneously in the body with minor surgery. The success of the implant is dependent upon the ability of the ceramic to resorb within the body due to its chemical composition and microstructure. The composition, processing parameters and final ceramic microstructure are considered for each drug and the physiological system receiving the drug. Typically, the drug is introduced into the ceramic material by immersing the ceramic material into the drug or by simply filling the ceramic body with a drug.

The resorption of the implant ceramic allows for implantation of a pharmaceutical delivery system that can last for an identifiable length of time before resorbing in vivo and therefore, does not have to be removed. This eliminates the need for medication requiring daily injections and provides a continuous and sustained dosage level.

The present invention is more fully illustrated by the following non-limiting Examples.

EXAMPLE 1

Three separate 50g zinc based ceramics were prepared by mixing zinc oxide, calcium oxide and phosphorus pentoxide powders in a v-blender in the weight ratios shown in Table 1.

TABLE 1

| Compositions | Oxides | | |
| --- | --- | --- | --- |
| | ZnO | CaO | $P_2O_5$ |
| A | 50 | 30 | 20 |
| B | 40 | 40 | 20 |
| C | 30 | 30 | 40 |

The above mixtures were calcined for five days at 700° C. in a furnace. After calcining, the samples were cooled for twenty-four hours and examined for their physical disposition. Composition A was hard, green in color and had the consistency of cancellous bone. Composition B was more brittle, crushable and lighter in color than composition A. Composition C was white comparable to aluminum based ceramics and had a very hard consistency. Calcining at 1300° C. also gave the same results.

Compositions A and B were evenly colored and retained their shape after calcining indicating that the powders had mixed homogenously and calcined evenly. On the other hand, composition C melted to a glassy material in the crucible. Because the melting point of the phosphorus pentoxide is in the range of 580° to 585° C. and the melting points of zinc oxide and calcium oxide are 1975° and 2614° C. respectively, it is obvious that the higher content of $P_2O_5$ (40%) was responsible for the mixture melting. The three compositions were subsequently recovered from the calcining crucibles and ground by hand to a powder state. The powder was sized by means of an automatic sieving system into three samples: less than −37, 53–105 and 210–350 micron particles.

EXAMPLE 2

The three samples of particles obtained from Example 1 were mixed with alph-ketoglutaric (AKG) or malic acids (MA) in 2:1 weight ratios and observed for setting and hardening characteristics on addition of distilled water.

TABLE 2

| Particle Size | Setting Agent | Time | Comments |
| --- | --- | --- | --- |
| −37 microns | malic acid | 22 sec. | Reached a wet solid state in 33–45 seconds. Became very hard after 1 hour. |
| −37 microns | alpha-ketoglutaric acid | 30 sec. | Wet solid state in 33–45 seconds. Harder than number 1. More homogenous but lower in final hardness. |
| 53–105 microns | malic acid | 40 sec. | Not as hard as number 1 even after 24 hours. |
| 53–105 microns | alpha-ketoglutaric acid | 60 sec. | Not as hard as number 1 but was more homogenous. |
| 210–350 microns | malic acid | 50 sec. | Very brittle. |
| 210–350 microns | alpha-ketoglutaric acid | 90 sec. | Very porous and brittle |

The ceramic-MA (1 gram) cements or grouts needed 0.3 ml distilled water to set whereas the ceramic-AKG cements or grouts required 0.4 ml distilled water to set. The set point is defined as the state when the ceramic composite mixture stops flowing on the deep well slide on tilting.

The ceramic-AKG cements or grouts appeared to yield more homogenous set cements or grouts because the AKG dissolved more evenly than MA. The increase in particle size was associated with a decrease in mechanical strength and an increase in porosity. The ceramic-MA composites had a very fast setting time. The ceramic-MA composites would be excellent for applying directly to an open wound in powdered state and letting the mixture set in situ. Ceramic-polyfunctional carboxylic acid cements or grouts act as efficient hemostatic agents.

EXAMPLE 3

In vitro studies were conducted on ceramics made by mixing the three oxides in the weight ratios as shown in Table 3.

TABLE 3

| Compositions | Oxides | | |
| --- | --- | --- | --- |
| | ZnO | CaO | $P_2O_5$ |
| D | 48 | 32 | 20 |
| E | 40 | 40 | 20 |
| F | 30 | 40 | 30 |

The mixtures were calcined at 1315° C. for twelve hours and sintered at 1300° C. Since the smaller particles gave the best setting times and hardness, the sintered composite was ground and sieved to obtain −37 micron particles. The ceramic was mixed in a weight ratio of 2:1 with alpha-ketoglutaric acid. One gram of this composite had a setting time of two minutes when mixed with 0.6 ml of distilled water.

EXAMPLE 4

Zinc based ceramics were also prepared in half-inch cylindrical blocks by pressing the powders of Table 4 in a die at 2000 pounds for ten seconds.

TABLE 4

| Compositions | Oxides | | |
|---|---|---|---|
| | ZnO | CaO | $P_2O_5$ |
| G | 50 | 30 | 20 |
| H | 48 | 32 | 20 |
| I | 40 | 40 | 20 |
| J | 30 | 30 | 40 |

Green shape composed of 3.5 gram ceramic material and 0.0875 gram solid polyvinyl alcohol was then sintered at 1400° C. for 36 hours and cooled for 24 hours.

Ceramic cylinders made from Composition J melted due to the presence of excessive amounts of phosphorus pentoxide. The other three compositions yielded strong and viable ceramics quite comparable and probably superior to the aluminum based ceramic cylinders. Morphological gross examination of tne zinc based ceramic cylinders suggested that they have higher strength than the aluminum based ceramic cylinders of similar dimensions.

EXAMPLE 5

A dissolution study was conducted with the ceramic-polyfunctional carboxylic acid cements or grouts of Example 3. Cement or grout samples (0.33±0.0025 g) were placed in 50 ml Trizma-HCL buffer (pH 7.39 at 37° C.) in a serum bottle at 37° C. in an oscillating water bath for durations of 1, 2, 4, 6, 8, 10 and 14 days. Triplicates of the Trizma buffer controls were included. At the end of each duration, the buffer was analyzed for $Zn^{++}$, $Ca^{++}$ and inorganic phosphorus content. The data obtained is shown in Tables 5–7. The highest release of ions occurred during the first 24 hours of the experiment.

TABLE 5

| | Calcium Content (ppm) | | |
|---|---|---|---|
| Time (days) | Composition D | Composition E | Composition F |
| 1 | 2966 | 4233 | 4066 |
| 2 | 2933 | 4266 | 4000 |
| 4 | 2966 | 4800 | 3966 |
| 6 | 3066 | 4266 | 4133 |
| 8 | 3066 | 4300 | 3933 |
| 10 | 2966 | 4266 | 3966 |
| 14 | 2933 | 4066 | 3900 |

TABLE 6

| | Zinc Content (ppm) | | |
|---|---|---|---|
| Time (days) | Composition D | Composition E | Composition F |
| 1 | 5500 | 4030 | 3930 |
| 2 | 5100 | 4030 | 3900 |
| 4 | 4930 | 4030 | 3760 |
| 6 | 5030 | 4030 | 3700 |
| 8 | 5760 | 4530 | 4160 |
| 10 | 4600 | 3830 | 3160 |
| 14 | 4630 | 3530 | 1830 |

TABLE 7

| | Phosphorus Content (ppm) | | |
|---|---|---|---|
| Time (days) | Composition D | Composition E | Composition F |
| 1 | 4000 | 3300 | 3350 |
| 2 | 3950 | 3275 | 3375 |
| 4 | 4025 | 3275 | 3400 |
| 6 | 4050 | 3280 | 3325 |
| 8 | 4075 | 3250 | 3375 |
| 10 | 4075 | 3200 | 3350 |
| 14 | 4325 | 3225 | 3275 |

EXAMPLE 6

Since the highest release of ions occurred during the first 24 hours in Example 5, the experiment was repeated and the observations were made at each hour for 24 hours. Release of the three ions from the ceramic occurred at approximately the same rate during this period as shown in Tables 8–10. However, the zinc may be released at a slightly slower rate.

TABLE 8

| | Calcium Content (ppm) | | |
|---|---|---|---|
| Time (hours) | Composition D | Composition E | Composition F |
| 1 | 1200 | 1030 | 1660 |
| 2 | 2400 | 3730 | 2730 |
| 3 | 3560 | 3930 | 2830 |
| 4 | 3730 | 4600 | 2850 |
| 5 | 3700 | 3860 | 4000 |
| 10 | 3500 | 4230 | 3800 |
| 18 | 3260 | 3960 | 3660 |
| 24 | 3460 | 4330 | 3830 |

TABLE 9

| | Zinc Content (ppm) | | |
|---|---|---|---|
| Time (days) | Composition D | Composition E | Composition F |
| 1 | 2100 | 160 | 630 |
| 2 | 2630 | 730 | 730 |
| 3 | 3100 | 1230 | 1360 |
| 4 | 3130 | 2000 | 1930 |
| 5 | 4560 | 2460 | 2960 |
| 10 | 5930 | 4000 | 3880 |
| 18 | 5930 | 4200 | 3860 |
| 24 | 5930 | 4300 | 3880 |

TABLE 10

| | Phosphorus Content (ppm) | | |
|---|---|---|---|
| Time (days) | Composition D | Composition E | Composition F |
| 1 | 1600 | 560 | 2200 |
| 2 | 3030 | 2260 | 2530 |
| 3 | 3130 | 2930 | 2700 |
| 4 | 3030 | 3230 | 3100 |
| 5 | 3030 | 2930 | 3330 |
| 10 | 3030 | 2960 | 3360 |
| 12 | 3040 | 2930 | 3360 |
| 18 | 2900 | 2980 | 3360 |
| 24 | 2900 | 2960 | 3430 |

EXAMPLE 7

Three different mixtures of metal oxides were prepared in the ratios shown in Table 11. After blending the powders of various oxides, one gram of mixed powder was mixed with 0.3 grams of polyvinyl alcohol (PVA).

TABLE 11

| Group Number | ZnO (%) | CaO (%) | $P_2O_5$ (%) |
|---|---|---|---|
| 1 | 48 | 32 | 20 |
| 2 | 40 | 40 | 20 |
| 3 | 30 | 40 | 30 |

Thereafter, the total of 1.03 grams of the composite including the three oxides and binder was compressed into a hollow cylindrical capsule (green shape) by means of a die at a load of 7000 lbs by a French Press. The green shape of ZCAP capsules was then hardened by sintering at 1250° C. for 36 hours.

Three capsules of each oxide mixture plus the polyvinyl alcohol binder were made in this manner to make a total of 9 capsules.

The reservoirs of each capsule were then filled with methylene blue. Groups 1 and 3 contained 40 milligrams in each capsule whereas the reservoir size of the capsules in group 2 limited the amount to 30 milligrams of methylene blue. The capsules were then sealed with a medical silicone adhesive from Dow Corning.

The capsules were then placed in 100 ml of distilled water and placed in a 37° C. shaker bath. Absorbance readings were taken at 660 nm every hour for the first 7 hours and then lengthening periods thereafter to determine the amount of methylene blue released. The results are as shown in Tables 13-15.

TABLE 13

The Release of Methylene Blue from Ceramic Capsules (Group 1)

| Time (hours) | Release (MG/100 ml) |
| --- | --- |
| 1 | 0.009 +/−0.0040 |
| 2 | 0.2294 +/−0.0793 |
| 3 | 0.5147 +/−0.1559 |
| 4 | 0.5614 +/−0.0412 |
| 5 | 0.6584 +/−0.0022 |
| 6 | 0.6801 +/−0.0603 |
| 7 | 0.8375 +/−0.0540 |
| 14 | 0.9470 +/−0.0702 |
| 100 | 2.2470 +/−0.2454 |
| 116 | 2.5300 +/−0.0574 |

TABLE 14

The Release of Methylene Blue from ceramic capsules (group 2).

| Time (hours) | Release (MG/100 ml) |
| --- | --- |
| 1 | 0.0022 +/−0.000 |
| 2 | 0.1110 +/−0.009 |
| 3 | 0.2190 +/−0.000 |
| 4 | 0.2220 +/−0.030 |
| 5 | 0.2310 +/−0.002 |
| 6 | 0.2400 +/−0.004 |
| 7 | 0.2570 +/−0.005 |

TABLE 15

The Release of Methylene Blue from ceramic capsules (group 3).

| Time (hours) | Release (MG/100 ml) |
| --- | --- |
| 1 | 0.0292 +/−0.0014 |
| 2 | 1.3500 +/−0.1200 |
| 34 | 15.260 +/−2.9900 |
| 100 | 16.770 +/−0.5370 |
| 116 | 24.350 +/−0.6090 |

The capsules composed of zinc oxide, calcium oxide and phosphorous pentoxide in the ratio of 30:40:30 of group 3 provided the best delivery mechanism for methylene blue. The data from group 2 suggest a possibility that these ZCAP ceramics in the ratio of 40:40:20 may have very large pores providing a quick delivery of the contained substance accompanied by a complete disintegration of the capsules. These large pores may point to the possibility of delivery of substances composed of very large molecules. Although the capsules in group 1 did not release much methylene blue, this ratio of ZCAP of 48:32:20 with decreased pressure loads in forming the capsule should provide a long term slow delivery mechanism. The proper manipulation of compression load, sintering time and temperature, and powder mixture ratios can give ceramics characteristics making them appropriate for use in drug delivery devices or orthopaedic surgery.

EXAMPLE 8

Ceramics were produced to demonstrate the ability of each blend (30:30:40; 30:40:30; 40:20:20; 48:32:20 and 50:30:20) to form solid cylinders. A ½" solid cylinder die was filled with a mixture of 3.5 g ceramic (<37 micron particles) and 0.0875 g polyvinyl alcohol (<100 micron particles) and compressed in a French press at 2000 lbs load for 10 seconds. The "green shape" was removed from the die and dessicated overnight. The ceramics were then placed in aluminum oxide crucibles and sintered for 3 hours at 800° C. and then at 1400° C. for 33 hours. The resultant ceramic cylinders had compressive strength of 8 to 9 MPa. Upon impregnation with polylactic acid, the compressive strength increased to 44 to 46 MPa.

Having described the invention in detail and by reference to preferred embodiments thereof, it will be apparent that modifications and variations are possible without departing from the scope of the invention defined in the appended claims.

What is claimed is:

1. A bioceramic comprising, based on the total weight of said bioceramic, about 10 to 50% by weight zinc oxide or zinc sulfate or mixtures thereof, about 30 to 40% by weight calcium oxide, and about 10 to 40% by weight phosphorus pentoxidel, said bioceramic being aluminum free.

2. The bioceramic of claim 1 which comprises said zinc oxide, said calcium oxide and said phosphorus pentoxide.

3. The bioceramic of claim 2 wherein said ceramic has a particle size of about 1 to 400 microns.

4. The bioceramic of claim 3 wherein said bioceramic comprises, based on the total weight of said bioceramic, about 30 to 50% by weight zinc oxide, about 30 to 40% by weight calcium oxide, and about 20 to 40% by weight phosphorus pentoxide.

5. A surgical cement composition comprising a powdered bioceramic and a setting agent, said bioceramic comprising, based on the total weight of said bioceramic, about 10 to 50 wt % zinc oxide or zinc sulfate or mixtures thereof, about 30 to 40 wt % calcium oxide, and about 10 to 40 wt % phosphorus pentoxide, said bioceramic being aluminum-free.

6. The surgical cement composition of claim 5 wherein said bioceramic comprises said zinc oxide, said calcium oxide and said phosphorus pentoxide.

7. The surgical cement composition of claim 6 wherein said setting agent is selected from the group consisting of amines, amino acids, polyfunctional carboxylic acids, polymers reactive with said bioceramic and mixtures thereof.

8. The surgical cement composition of claim 7 wherein said amine is selected from the group consisting of carbodiimides; N,N-dimethyl-p-toluidine; N,N-diethyl-p-toluidine; N,N-dimethylaniline; N,N-diethylaniline and mixtures thereof.

9. The surgical cement composition of claim 7 wherein said amino acid is selected from the group consisting of alanine, arginine, asparagine, cysteine, glutamine, glycine, histidine, isoleucine, leucine, lysine, methionine, phenylalanine, proline, serine, threonine, valine and mixtures thereof.

10. The surgical cement composition of claim 7 wherein said polyfunctional carboxylic acid is selected from the group consisting of aconitic, alpha-ketoglutaric, citraconic, citric, fumaric, glutaconic, itaconic, maleic, malic, pyruvic, oxalic, succinic, tartaric and mixtures thereof.

11. The surgical cement composition of claim 7 wherein said bioceramic has a particle size of about 1 to 400 microns.

12. The surgical cement composition of claim 11 wherein said cement further comprises a calcium salt.

13. The surgical cement composition of claim 7 wherein said polymer is selected from the group consisting of polylactic acid, polyacrylic acid, and polymethacrylic acid.

14. The surgical cement composition of claim 5 wherein the ratio of said resorbable ceramic to said setting agent based on the weight of said cement composition is about 1:1 to 3:1.

15. An implant comprising, based on the total weight of said implant, about 10 to 50% by weight zinc oxide or zinc sulfate or mixtures thereof, about 30 to 40% by weight calcium oxide, and about 10 to 40% by weight phosphorus pentoxide, said implant being essentially non-toxic and bioabsorbable, said implant also being aluminum-free.

16. The implant of claim 15 wherein said implant comprises said zinc oxide, said calcium oxide and said phosphorus pentoxide.

17. The implant of claim 16 which is formed by the process comprising the steps of:

mixing said oxides and compressing said mixture, calcining said mixture at about 700° to 1300° C. for about 24 to 36 hours, powdering said calcined mixture and sieving said mixture to obtain particles of a size from about 1 to 50 microns, mixing said mixture with a binder and compressing at a pressure of about 2000 to 20,000 pounds total load and sintering said mixture.

18. The implant of claim 16 wherein after sintering, said implant has a pore size of about 1 to 400 microns.

19. The implant of claim 18 wherein said implant, based on the total weight of said implant, comprises about 30 to 50% by weight zinc oxide, about 30 to 40% by weight calcium oxide, and about 20 to 40% by weight phosphorus pentoxide.

20. A bioceramic material comprising, based on the total weight of said bioceramic, of from about 30 to 50% by weight zinc oxide, about 30 to 40% by weight calcium oxide, and from about 20 to 40% by weight phosphorus pentoxide, said bioceramic having a particle size of about 1 to 400 microns.

21. An implant comprising, based on the total weight of said implant, about 30 to 50% by weight zinc oxide, about 30 to 40% by weight calcium oxide, and about 20 to 40% by weight phosphorus pentoxide, said implant having a pore size of about 1 to 400 microns.

* * * * *